United States Patent [19]

Braun

[11] 4,158,958

[45] Jun. 26, 1979

[54] CONTROLLED SENSITIVITY MONITORING DEVICES

[75] Inventor: David L. Braun, Lake Elmo, Minn.

[73] Assignee: Minnesota Mining and Manufacturing Co., Saint Paul, Minn.

[21] Appl. No.: 913,945

[22] Filed: Jun. 9, 1978

[51] Int. Cl.² ............................................. G01N 31/00
[52] U.S. Cl. ........................................... 73/23; 422/88
[58] Field of Search ........................ 73/23; 422/88, 53

[56] References Cited

U.S. PATENT DOCUMENTS

| | | | |
|---|---|---|---|
| 3,950,980 | 4/1976 | Braun | 73/23 |
| 3,985,017 | 10/1976 | Goldsmith | 73/23 |

Primary Examiner—S. Clement Swisher
Attorney, Agent, or Firm—Cruzan Alexander; Donald M. Sell; Carolyn A. Bates

[57] ABSTRACT

A controlled sensitivity device for measuring the amount of a selected component in fluid mixture is disclosed. A collecting layer is disposed within a chamber into which the fluid mixture is allowed to diffuse. Sensitivity of the device is controlled by varying the ratio of the chamber entrance area to the frontal surface area of the collecting layer and the shape of the chamber to cause divergence of convergence of molecules within the chamber.

13 Claims, 17 Drawing Figures

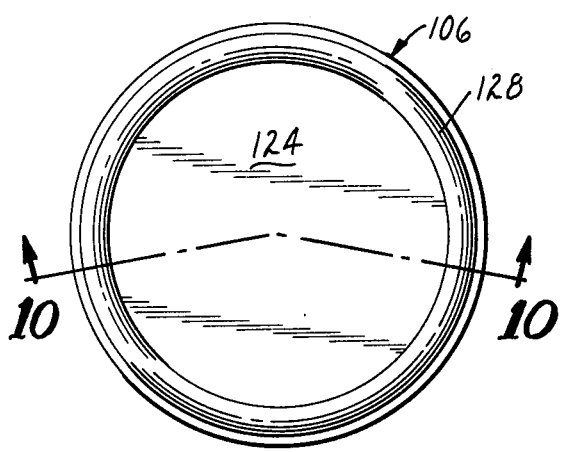
FIG. 9
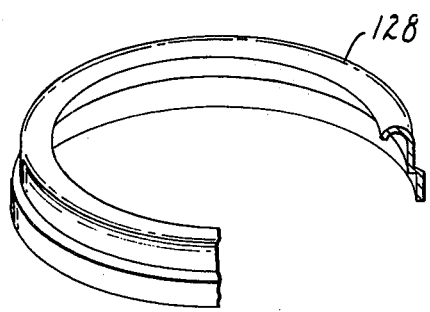
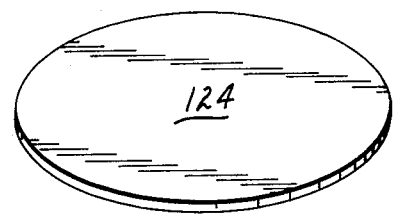
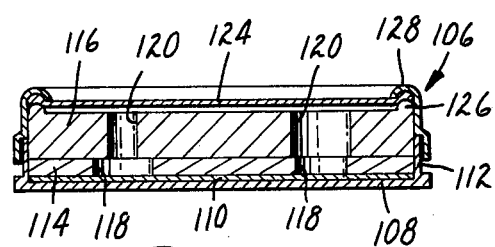
FIG. 10
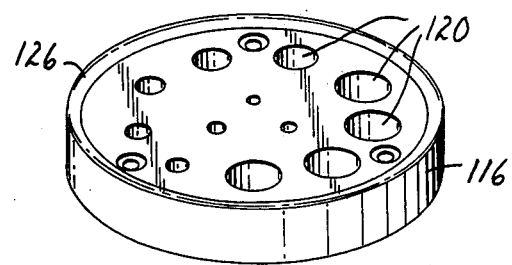
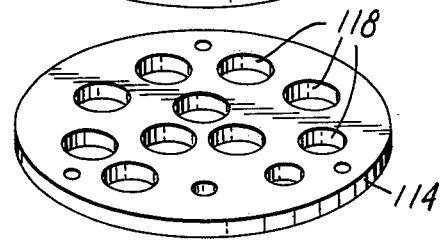
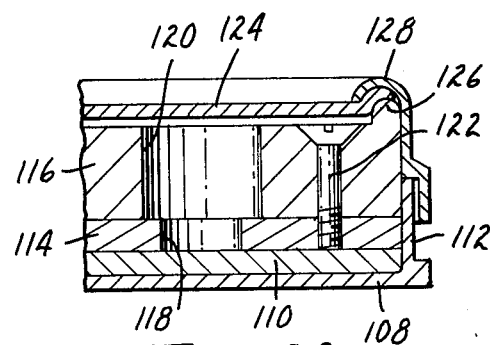
FIG. 11
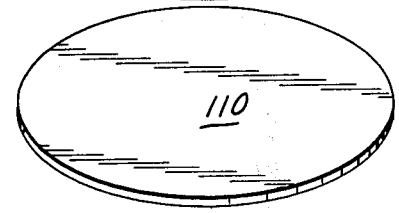
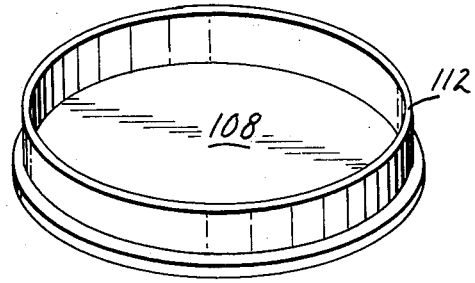
FIG. 12

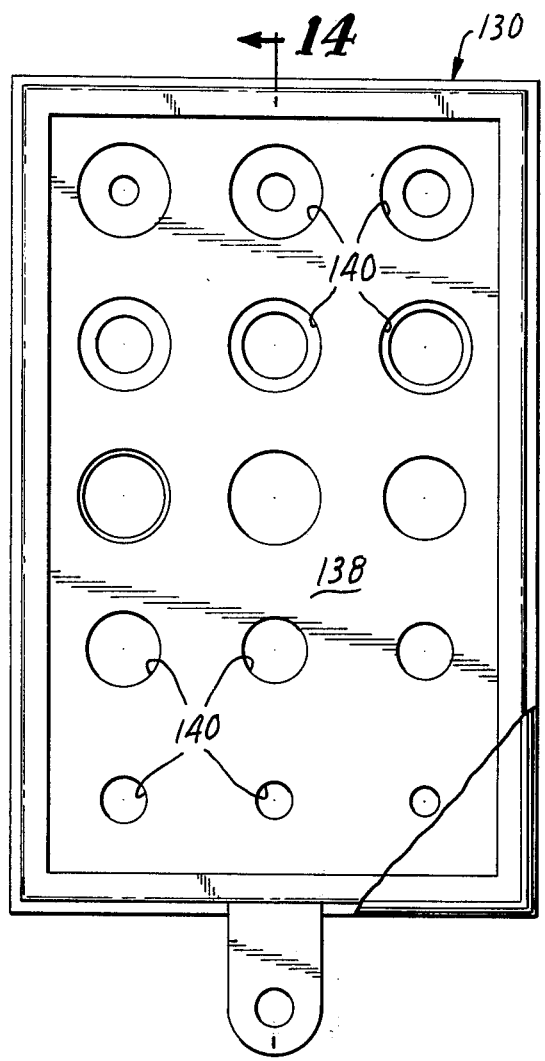
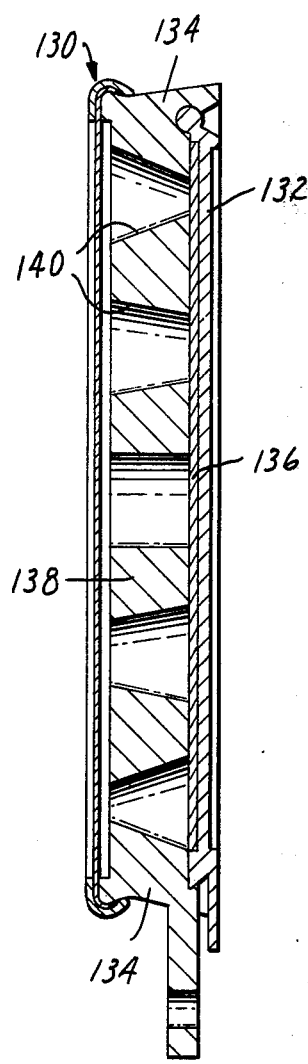
FIG.13  FIG.14
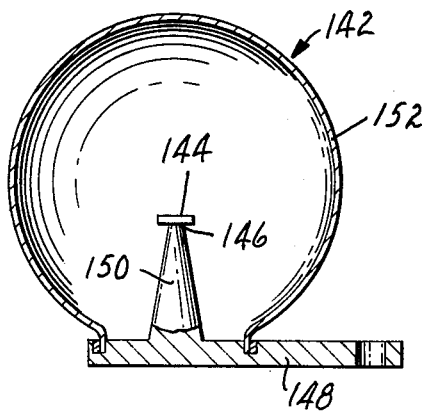
FIG.15

CONTROLLED SENSITIVITY MONITORING DEVICES

This invention relates to devices for measuring the amount of at least one selected component of a fluid mixture. More specifically, it relates to monitoring devices for the quantitative detection of materials of environmental consequence in fluids such as air, water, etc.

In recent years, increasing emphasis has been placed on providing industrial workers with an environment which is free from hazardous levels of toxic materials. The Occupational Safety and Health Administration (OSHA) of the United States Government, Department of Labor has issued regulations requiring that industrial environments be monitored to determine the levels of worker exposure to various hazardous gases. Standards have been established which limit the amount of a particular hazardous gas to which a worker may be exposed during a given time period.

In order to determine the amount of an individual's exposure to a particular contaminant, samples of the fluid mixture containing the contaminant must be taken. Generally, such samples have been taken using sampling pumps or evacuated volumes to move a defined volume of contaminant-containing fluid through an appropriate filter or into a container. This sampling process was greatly simplified and improved by the introduction of diffusional controlled monitors such as those described in U.S. Pat. Nos. 3,924,219 and 3,950,980 owned by the same assignee as the present application. These devices utilize Brownian motion to control sampling into a collection medium. They are light weight, unobtrusive, economical and require no external power source. These devices comprise an enclosure containing a collecting layer which selectively removes or otherwise interacts with the contaminant or contaminants from the ambient fluid, and one or more porous attenuating layers across the opening of the enclosure. The ambient fluid enters the device by diffusion through the attenuating layer and the selected component diffuses through a placid layer of fluid to the collecting layer. The placid layer occupies the volume within the enclosure separated from the ambient fluid by the outer attenuating layer. The attenuating layer(s) and placid layer(s) of fluid significantly reduce the undesirable effects caused by fluid moving relative to the device. After the selected contaminants have been collected by the collecting layer over a measured time period, the concentration of the contaminant in the ambient fluid can be determined by analysis of the collecting layer using a variety of conventional techniques depending upon the chemical nature of the collecting layer and the contaminant being monitored.

In a diffusional controlled monitoring device of the type described above, it is desirable to maximize: (1) velocity independence; (2) sensitivity control over wide extremes of contaminant concentration; and (3) uniformity of molecular or atomic flux at the collecting layer. The prior art devices do not provide the optimum combination of all three of these properties. Particularly, prior art devices do not provide high sensitivity (for use in environments of low concentration) without also decreasing velocity independence.

Velocity independence in a diffusional monitor refers to the degree of freedom from the effects of variable fluid velocity in the region just adjacent to the monitor.

An understanding of the importance of velocity independence may be gained by considering the following.

Molecules being sampled by a diffusional monitor must pass through (1) an external boundary layer having a variable resistance to molecular passage, and (2) an internal placid layer having a relatively fixed resistance to molecular passage.

The external boundary layer is attached to and outside of the outermost attenuating layer and the resistance of this layer varies with changes in fluid velocity. The internal placid layer is contained between the outermost attenuating layer and the collecting layer and its resistance remains constant if the layer remains placid.

If the largest variations in external boundary layer resistance are small with respect to the placid layer or internal resistance, the monitor has high velocity independence. By increasing the ratio of internal to external resistance, one can increase velocity independence. In the present invention velocity independence is increased without sacrificing molecular flux at the collecting layer.

In prior art devices such as those described in U.S. Pat. No. 3,950,980, control over sensitivity is provided by varying the attenuating layers and the placid layer thickness. More restrictive attenuating layers such as porous plates of particulate material reduce the amount of fluid entering the device, thus reducing sensitivity. Less restrictive attenuating layers and reduced placid layer thickness allow more fluid to enter the device, and, consequently, increase sensitivity. However, increased sensitivity through the use of less restrictive attenuating means and reduced placid layer thickness was attained at the expense of velocity independence.

In the present invention, means for achieving high sensitivity without sacrificing velocity independence have been discovered. Further, means for reducing sensitivity without using restrictive attenuating means have been discovered. Therefore, wide-ranging control over device sensitivity can now be realized without sacrificing velocity independence. This wide-ranging sensitivity control makes it possible to make a multiple chamber monitor with each chamber having a different sensitivity and with each collecting layer capable of being analyzed separately.

In the prior art, the use of restrictive attenuating means such as porous plates and/or diffusion gratings, although adequate for many applications, sometimes resulted in non-uniform molecular flux at the collecting layer, that is, the collection of molecules of contaminant would be high in some areas of the collecting layer and lower in others. The present invention provides for uniform flux consistent with wide-ranging sensitivity control and velocity independence.

In summary, the present invention provides monitoring devices in which the sensitivity of the device can be adapted to wide concentration ranges of the environmental contaminant being monitored. Further, the present invention provides means for consistent smooth deposition of collected contaminant. At any given contaminant concentration, the present invention provides for velocity independence while maintaining selectability over the magnitude of molecular flux at the collecting layer. Furthermore, the present invention may be utilized to provide multi-chamber devices in which the sensitivity varies from chamber to chamber. Such devices are accurate over a broad range of contaminant concentrations. If the collecting layer(s) of such multi-chamber devices are provided with a visual read-out such as a calibrated color change, it is possible for the user to observe his level of exposure to a particular contaminant by the progression of color change from the most sensitive chambers to the least sensitive chambers.

When sampling a component of fixed concentration in a fluid, the sensitivity of a monitor is determined by the molecules collected or reacted per unit area. The greater the number of molecules per unit area, the greater the sensitivity of the monitor, and the sensitivity decreases as fewer molecules per unit area are collected on the collecting layer. The molecular flux (J) of the measured component onto the collecting layer in a diffusional monitoring device is related to the sensitivity of the device.

The molecular flux (J) is defined as the rate the molecules arrive per unit area at the collecting layer.

$$J = (1/A)(dn/dt)$$

Upon integrating the above expression, the molecules collected per unit area in time t over area A is given by the following:

$$n/A = Jt + K$$

where n is the total number of molecules collected and K is an integration constant. Therefore, the total number of molecules collected or interacted per unit area is directly proportional to the sensitivity of the monitor and also directly proportional to the molecular flux at the collecting layer of the monitor. The detection sensitivity of diffusional monitors can then be varied by controlling the molecular flux of the component being measured onto the collecting layer. A monitoring device such as in FIG. 2 has a cylindrical enclosure through which the molecules must diffuse before reaching the collecting layer. The molecular flux (J) (molecules/sec/cm$^2$) on the collecting layer in such a device can be expressed by Fick's First Law of Diffusion $$J = D(dc/dx)$$

where D is the binary diffusion coefficient and dc/dx is the concentration gradient within the enclosure. At the entrance of the diffusional enclosure where $x=o$, the concentration, C, is substantially equal to the ambient concentration, $C_i$. At the collecting layer where $x=l$, where l is the thickness of the enclosure, the concentration is $C_o$. The above expression can be integrated in one dimension to give the following:

$$J = (C_i - C_o)D/l$$

Thus, the molecular flux (J) is inversely proportional to the thickness (l) of the diffusional enclosure and directly proportional to the difference in the concentration ($C_i$) at the entrance and the concentration ($C_o$) at the collecting layer of the diffusional enclosure. When using such monitoring devices to sample fluid with a fixed concentration ($C_i$) from the environment, the thickness (l) of the diffusional enclosure is one means of controlling the molecular flux (J) on the collecting layer and therefore the sensitivity of the monitor.

According to the present invention, the molecular flux onto the collecting layer, and therefore the sampling sensitivity can be controlled by varying the geometric shape of the diffusional chamber or passageway immediately adjacent to the collecting layer and/or the corresponding collecting layer area and chamber-entrance area. In the cylindrical diffusional enclosure having smooth vertical side walls as illustrated in FIG. 2, diffusion is one-dimensional because the gradient of molecular concentration is along the axis of thickness. If the diffusional enclosure does not have smooth vertical side walls, the diffusion will occur in more than one dimension because the gradient of the concentration will be in more than one direction.

These multi-directed gradients have been present in prior art devices such as those described in U.S. Pat. No. 3,950,980 to the extent that they occurred within the interior of the porous attenuating layers used in prior art monitors. In these cases, however, the effect was always in the direction of reducing molecular flux at the collecting or interaction layer, and the presence of the attenuating layer sometimes caused non-uniform molecular deposition or interaction. In the present invention, we find that by controlling (1) the size and shape of the chamber, and (2) the ratio of collecting layer area to chamber entrance area, one can attain either an increase or a decrease in molecular flux and therefore sensitivity at the collecting layer and also consistently achieve uniform molecular flux and velocity independence. Thus various single chamber monitors can be made at accommodate wide extremes in environmental concentration.

Although the sensitivity control provided by the invention can be usefully employed in single chamber monitors, it is especially useful in multi-chamber devices in which the sensitivity is increased in controlled increments from chamber to chamber.

According to the invention, devices are provided for measuring the amount of at least one selected component of a fluid mixture. A collecting layer having a frontal surface area for collecting the selected components is present in the device. The collecting layer is supported by a base. The collecting layer may serve as the base in certain cases where the layer is self-supporting and where contact with the ambient fluid occurs only within the chamber. The collecting layer is enclosed by barrier means which define at least one chamber having an entrance through which the fluid mixture diffuses into the chamber and in which the collecting layer is disposed. A substantially placid layer of fluid is provided within the chamber. The ratio of the chamber entrance area to the frontal surface area of the collecting layer is predetermined to provide a measuring device having a non-linear concentration gradient of the selected component in the chamber and affording molecular transport through the chamber between the chamber entrance and the collecting layer which is one of convergence or divergence or both. In contrast, the nonselected components of the fluid may diffuse randomly into and out of the chamber.

When the ratio (r) of the chamber entrance area to the frontal surface area of the collecting layer is greater than one, and/or when the shape of the placid layer is such that molecular transport is converging, the molecules of contaminant entering the chamber are concentrated per unit area of the collecting layer. Such a device has increased sensitivity over a device in which (r) is equal to or less than one and is correspondingly more accurate in monitoring environments in which the concentration of contaminant is low. The term "chamber entrance area" as used herein refers to the planar area of the largest aperture at the chamber entrance. The term "frontal surface area" as applied to the collecting layer refers a one to one projection of the planar or apparent area and not to the actual surface area of the porous material which can be higher.

It has also been discovered that sensitivity of the device can be controlled without sacrificing smooth molecular deposition or velocity independence by varying the shape and consequently the internal resistance to molecular flux of the chamber of placid fluid adjacent the collecting layer. Devices in which the walls of the chamber generally form an acute angle with the plane of a given collecting layer have increased resistance and the molecular transport is divergent. Devices in which the walls of the chamber form an obtuse angle with the plane of the same size collecting layer have decreased internal resistance, increased sensitivity and convergent molecular transport. The walls of the chamber may also be curved to increase or decrease chamber resistance to molecular flux thereby decreasing or increasing sensitivity, respectively even when the ratio (r) of the chamber entrance area to collecting layer area is the same. Convergence or divergence of the chamber walls may also be accomplished in a step-wise manner as opposed to using smooth converging or diverging walls.

The term "chamber" as used herein specifically refers to the portion of the device between the collecting layer and the attenuating layer or the innermost attenuating layer if more than one are present. Channels within the attenuating layer or diffusion grating are not considered part of the "chamber" in the context of the present invention. Furthermore, the chamber does not necessarily extend the full distance from the collecting layer to the attenuating layer in all devices. In some devices, the attenuating layer is elevated slightly above the internal walls defining the chamber or chambers of the device in order to allow perimeter support for the attenuating layer and, in the case of multi-chamber devices, to allow the attenuating layer to serve more than one chamber. In such devices a shallow common entry area or vestibule is present which is not considered part of the chamber of the device.

DESCRIPTION OF THE DRAWINGS

Further understanding of the invention will be facilitated by reference to the accompanying drawings wherein:

FIG. 2 is a sectional view taken along line 2—2 of FIG. 1;

FIG. 9 is a top plan view of a multi-chamber monitoring device;

FIG. 10 is a sectional view taken along line 10—10 of FIG. 9;

FIG. 11 is an expanded sectional view of a portion of the device shown in FIG. 10;

FIG. 12 is an exploded side perspective view of the monitoring device of FIGS. 9-11 illustrating the various parts;

FIG. 13 is a top plan view of multi-chamber monitoring device;

FIG. 14 is a sectional view taken along lines 14—14 of FIG. 13;

FIG. 15 is a section view of a single chamber monitoring device having very high sensitivity.

The monitoring device of the present invention is adapted for use in measuring the amount of a selected component of fluid in a mixture. It is adapted to be worn by the individual or positioned in the environment where the selected components are being sampled.

Figure 1:
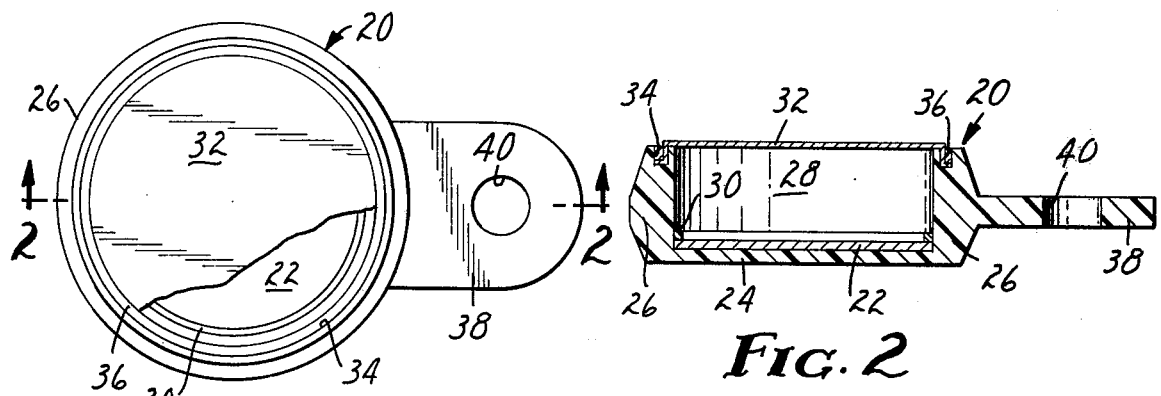
FIG. 1 is a top plan view of a prior art monitor such as that described in U.S. Pat. No. 3,924,219.

In FIGS. 1 and 2 a prior art monitoring device 20 is illustrated in which no means for increasing or decreasing sensitivity are provided other than increasing or decreasing the length of the cylindrical diffusion enclosure. The device 20 is generally circular in plan view and comprises a collecting layer 22 supported by base 24. Base 24 is continuous with sidewalls 26, and together with sidewalls 26 define an enclosure 28 containing collecting layer 22. The collecting layer is held in place in the bottom of enclosure 28 by retaining ring 30. Across the opening of the enclosure 28 is disposed a porous attenuating layer 32 which allows the fluid mixture to diffuse into enclosure 28 and significantly reduces the effects of external moving fluid on the accuracy of the device. The fluid inside enclosure 28 is substantially placid. Sidewalls 26 terminate at the free edges with a rim having a groove 34 into which retaining ring 36 releasably fits to seal and hold porous attenuating layer 32 in place. Extending from walls 26 on one side of the device is a flange 38, formed with an opening 40 permitting the device to be suitably fastened in a selected position, such as near the breathing zone of the worker.

The ratio (r) of the frontal surface area (chamber-entrance area) of the porous attenuating layer 32 and the frontal surface area of the collecting layer 22 is substantially one. Accordingly, there is no enchancement or diminution of molecular flux at the surface of the collecting layer.

Figure 3:
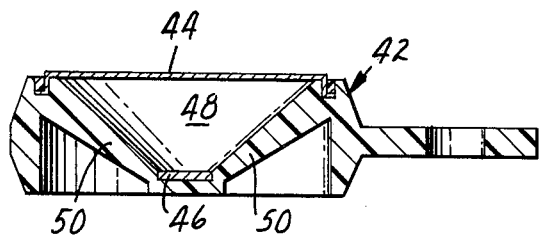
FIG. 3 is a sectional view of a monitoring device according to the present invention having increased sensitivity.
Figure 4:
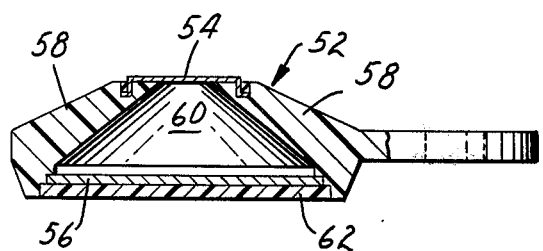
FIG. 4 is a sectional view of a monitoring device according to the present invention having decreased sensitivity.
Figure 5:
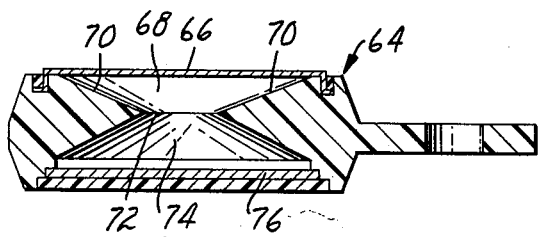
FIG. 5 is a sectional view of a device similar to that shown in FIG. 4 having a fluid gathering portion adjacent to the porous barrier.
Figure 6:
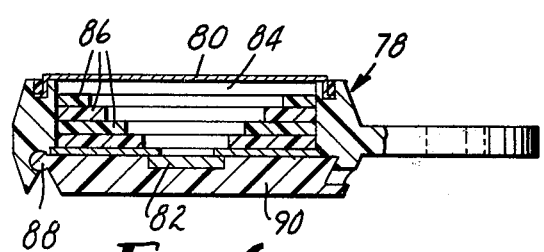
FIG. 6 is a sectional view of a monitoring device having walls which converge in step-wise manner toward the collecting layer.
Figure 7:
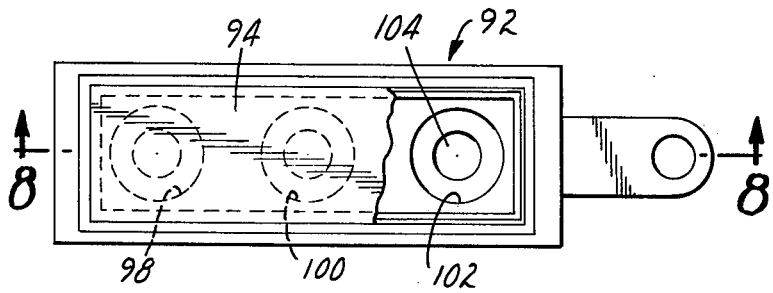
FIG. 7 is a top plan view of a multi-chamber monitoring device having varying sensitivity.

FIG. 3 illustrates a typical monitoring device according to the present invention which has enhanced sensitivity over the device of FIGS. 1 and 2. The device 42 is also essentially circular in plan view. It differs from the prior art device of FIGS. 1 and 2 in two primary respects. Firstly, the frontal surface area of the attenuating layer 44 is, for example, fifty times greater than the frontal surface area of collecting layer 46. Secondly, the shape of chamber 48 is modified by the addition of internal walls 50 which are not perpendicular to the plane of collecting layer 46, but rather form an obtuse angle with the collecting layer defining an inverted truncated conical chamber with the collecting layer 46 forming the top of the cone and the attenuating layer 44 forming the base of the cone. During the sampling period, molecular flux at the collecting layer is magnified over that of the device of FIGS. 1 and 2 by the ratio of the diameters of the chamber entrance to the frontal surface area of the collecting layer, e.g. about 700 percent. This device is useful in sampling contaminants from environments containing minute concentrations of contaminants. The surface area of collecting layer 46 is about two percent of that in the device of FIGS. 1 and 2. Consequently, the cost of the collecting layer in comparison to that of the device of FIG. 1 is greatly reduced. Furthermore, since the total molecular flow across the attenuating layer is much lower, e.g. 13 to 14 percent of the device of FIGS. 1 and 2, sampling errors due to ambient fluid velocities are greatly reduced. This reduction in errors arising from extremes in ambient fluid velocities results from the increase in the ratio of the internal to external resistance to molecular flow. The internal resistance to molecular flow is dependent upon the shape and size of the chamber adjacent to the collecting layer and (r). The external resistance is a function of the ambient fluid velocity and the area and thickness of the fluid boundary layer external and adjacent to the outermost attenuating layer of the device. As the ratio of internal resistance to external resistance is increased, errors due to ambient fluid velocities are reduced. The present invention combines reductions in velocity errors with increases in molecular flux at the collecting layer. In many inventions, some tradeoff of desirable attributes must be made. In the present invention, increased sensitivity and decreased velocity effects can be coexistent, and both are desirable.

The monitoring device 52 of FIG. 4 has decreased sensitivity over the device of FIGS. 1 and 2 and is designed for use in environments containing high concentrations of the contaminant being monitored. The chamber entrance area below attenuating layer 54 is, for example, 1/50th of the surface area of the frontal surface area of collecting layer 56. Sidewalls 58 are not perpendicular to collecting layer 56, but form an acute angle therewith. Walls 58 slant inward to define a truncated conical chamber 60 containing the collecting layer with the collecting layer 56 forming the base of the cone and the attenuating layer 54 forming the top of the cone. Collecting layer 56 is held in place by retaining ring 62. Compared to the device of FIGS. 1 and 2, the molecular flux at the collecting layer is greatly reduced in this particular illustration, by approximately 86 percent. One drawback with this device is that molecular flux in the portion of chamber 60 immediately adjacent attenuating layer 54 is approximately 7.0 times greater than that of the device of FIGS. 1 and 2. As a result of high molecular flux immediately adjacent the porous opening of the device, velocity sampling errors are increased, especially those associated with lower ambient velocities. The reason for this relates to the reason that velocity sampling errors for the device of FIG. 3 are diminished. In the case of the monitor of FIG. 4, the boundary layer resistance is much larger than that of the monitor of FIG. 3. Therefore, the ratio of placid layer or internal resistance to boundary layer or external resistance is smaller and velocity errors are correspondingly larger. The shape of the chamber 60 is such that smooth molecular deposition or interaction is obtained.

The monitoring device 64 of FIG. 5, like that of FIG. 4, is designed for sampling in environments containing high concentrations of the contaminant being monitored. It is slightly modified, however, to reduce velocity-induced sampling errors associated wtih the device of FIG. 4. The frontal surface area of attenuating layer 66 is increased to approximately that of the device of FIG. 1. Fluid entering the device through attenuating layer 66 first reaches a molecular gathering section 68 which is formed by internal walls 70 which slant inwardly from the rim to form an inverted truncated conical section having an aperture 72 at the top which opens into chamber 74 adjacent the collecting layer 76. The interior sidewalls of chamber 74 are slanted to form an acute angle with the plane of collecting layer 76. In this embodiment, the reduced area of the aperture 72 in relation to the frontal area of collecting layer 76 (e.g., a 1:49 ratio) results in decreased sensitivity. The velocity sampling error of this device is less than that of the device of FIG. 4 by approximately the amount of the percent increase in the frontal surface area of the attenuating layer 66. Molecular flux at the surface of the collecting layer 76 is reduced below that of the device of FIG. 4 because of the added molecular impedence caused by the gathering section 68.

The monitoring device 78 of FIG. 6 differs from the device of FIGS. 1 and 2 by having an attenuating layer 80 which has a significantly larger surface area than the frontal surface area of collecting layer 82. The sensitivity of the device is greatly increased over the sensitivity of the device of FIGS. 1 and 2. The sensitivity of this device is about the same as that of the device of FIG. 3, and the ratio of the chamber entrance area to the frontal surface area of the collecting layer is approximately the same. Chamber 84 has walls which converge through a series of five steps 86 from attenuating layer 80 to collecting layer 82. Internal resistance to molecular flux through the placid layer can be varied in at least two ways: (1) by changes in the placid layer geometry as in FIG. 3; and (2) by varying the frontal area of the collecting layer with respect to the chamber-entrance area. In the latter case, internal resistance can be increased by reductions in the frontal collecting layer area for a given chamber entrance area even though the placid layer volume remains the same. This increases sensitivity and reduces velocity errors. Device 78 of FIG. 6 is also provided with a hinge 88 on the base of the device allowing the base plate 90 to be opened for access to the collecting layer. If the collecting layer contains a chemical which changes color in response to a given amount of contaminant, the level of exposure may be read visually. Optionally, the base plate 90 of the device may be constructed of transparent material, e.g., an optically clear polymer, eliminating the need for a hinged base plate in visual read-out devices.

FIGS. 7 and 8 illustrate a multi-chamber monitoring device 92 in which sensitivity varies from chamber to chamber due to the shape of the chambers adjacent to the collecting layers. Attenuating layer 94 is perimeter supported and extends across the upper surface of the device. Fluid entering the device through the attenuating layer 94 enters vestibule 96 and then passes into one of the chambers 98, 100, or 102. Collecting layer 104 is disposed across the entire interior bottom of the device although only those portions of collecting layer 104 directly contacting chambers 98, 100, and 102 are utilized. The sensitivity of chamber 98 having a truncated ovate or "bullet" shape is surprisingly more sensitive than chamber 100 having a truncated conical shape which is in turn more sensitive than chamber 102 having a "trumpet" shape, i.e., having opposed convex walls in vertical cross section. It is believed that molecular flux at the surface of the collecting layer is amplified in chamber 98 over chambers 100 and 102 due to the decreased internal resistance of the chamber, i.e., the internal resistance of the placid layer through which molecules diffuse to contact the collecting layer. As chamber shape changes from chamber 98 to 100 to 102, the sensitivity is correspondingly decreased even though (r) remains the same.

FIGS. 9–12 illustrate another multi-chamber device according to the invention. The device 106 as shown in FIG. 9 is generally circular in plan view. In FIG. 12, the various parts of the device are shown in exploded view. The device comprises a base plate 108 which supports the collecting layer 110. Side walls 112 extend vertically from base plate 108 and define a shallow container having an open end. The individual chambers of the device are provided by plates 114 and 116, each containing a plurality of circular holes 118 and 120 respectively. The plates are aligned with one another by means of three aligning screws 122 shown in expanded view in FIG. 11. The holes 120 in plate 116 form the top portion of the chamber and some are larger and some are smaller in diameter than the corresponding holes 118 in plate 114 which form the lower portion of the chambers. As shown in sectional view in FIG. 10, the diameter of each of the holes in plate 114 determines the surface area of collecting layer in each chamber. The diameter of each hole in plate 116 determines the surface area at the entrance of each chamber. In some cases the hole in plate 114 is larger than the hole in plate 116 with which it is aligned. The chamber thus formed has decreased sensitivity. Likewise, in some cases the hole in plate 114 is smaller than the hole in plate 116 with which it aligns resulting in a chamber with increased sensitivity. The chambers are arranged so as to provide a step-wise increase in sensitivity. Attenuating layer 124 is placed over the top of plate 116 and spaced slightly therefrom by rim 126 extending from the perimeter if plate 116 forming a common vestibule. Retaining ring 128 fits around the component parts of the device and holds them together.

FIGS. 13 and 14 illustrate another embodiment of a multi-chamber device in which the individual chambers are formed in a single plate and are generally truncated conical in shape. The device 130 as illustrated is generally rectangular in plan view. It comprises a base plate 132 and side walls 134 defining a shallow container containing and collecting layer 136. The plate 138 which fits inside the container has a series of conical-shaped holes 140 therethrough providing a plurality of chambers. The ratio of the diameters of the openings on one side of the plate to the diameters of the openings on the other side of the plate varies from less than one, through unity to greater than one. Thus, the incline of the interior side walls varies from chamber to chamber. The chambers are arranged from most sensitive to least sensitive. If the collecting layer 136 contains a material which changes color in response to a predetermined amount of contaminant, it is possible to construct a device in which the collecting layer of each chamber progressively changes color as the user is exposed to more and more contaminant. The base plate 132 may be provided with a hinge as shown in FIG. 14 to allow the user to conveniently open the device to observe the color of each chamber. Alternatively, the base plate may be constructed of transparent material.

FIG. 15 illustrates a device 142 according to the invention having very high sensitivity. The collecting layer 144 is supported on substrate 146 which is elevated above the base plate 148 of the device by post-like member 150. The barrier or attenuating layer 152 surrounds the collecting layer to form a generally spherical chamber. The ratio of the surface area of the attenuating layer 152 to the surface area of collecting layer 144 as well as the internal resistance of the chamber defining the placid layer are such that sensitivity is maximized. This device is designed for use in environments containing very low concentrations of the contaminant being monitored.

Figure 16:
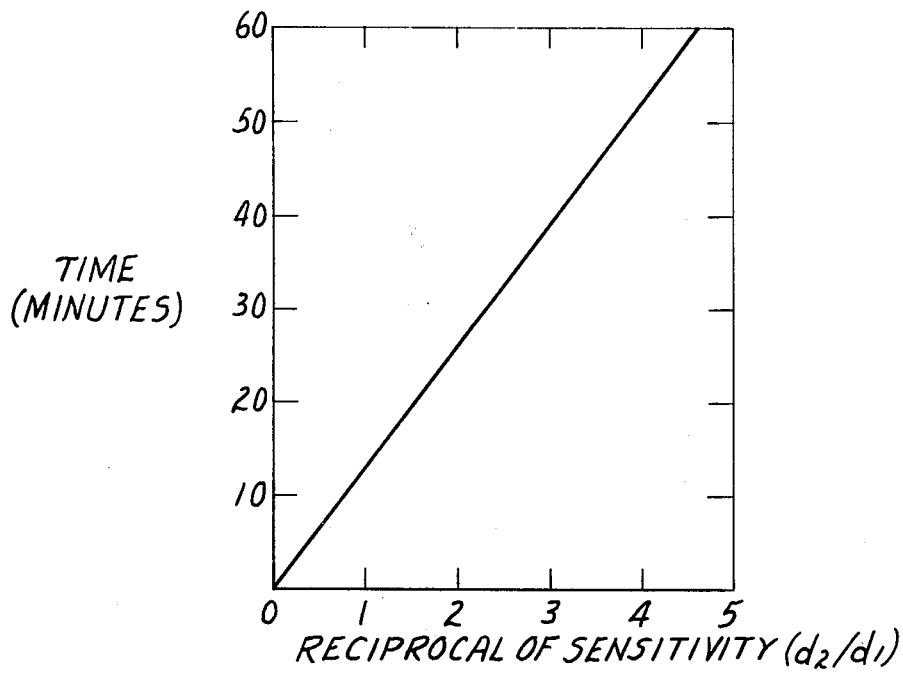
FIGS. 16-17 are curves obtained with various devices illustrating sensitivity as a function of controlled parameters.
Figure 17:
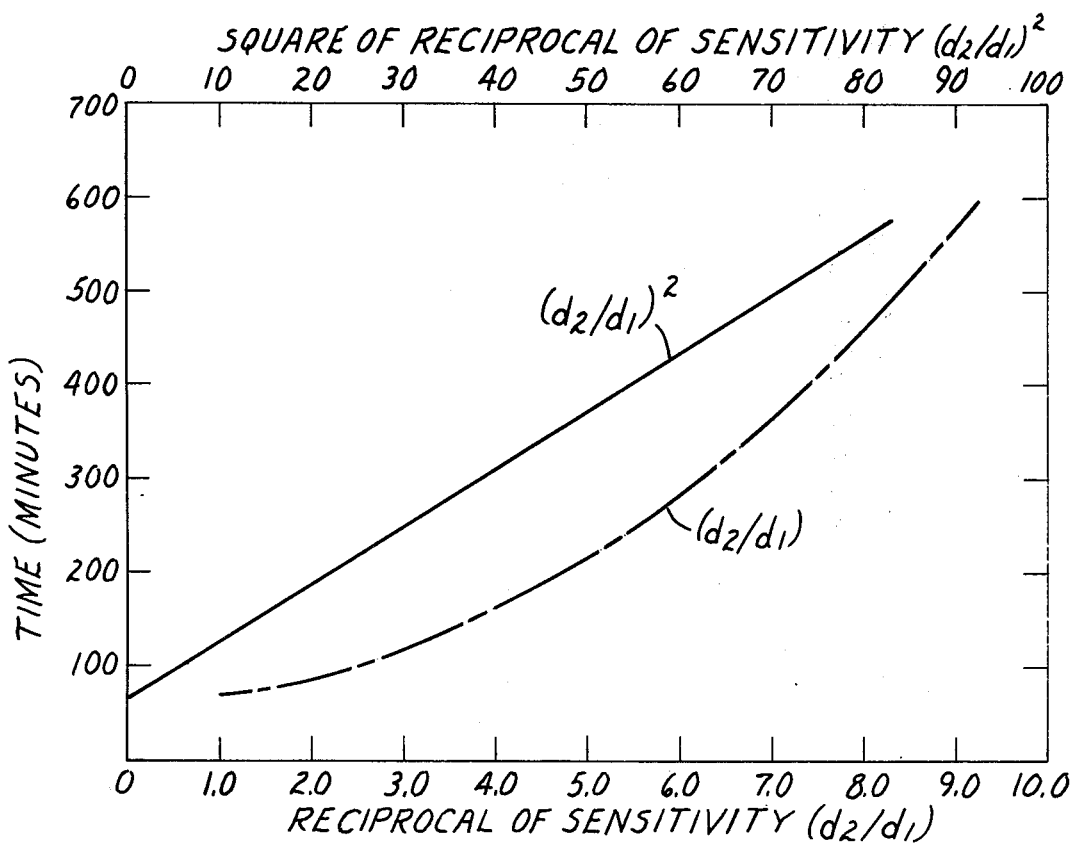

The curves shown in FIGS. 16–17 are described in conjunction with the examples below.

In use, the devices of the invention are exposed to a fluid mixture for a measured time period. The collecting layer of the device continuously picks up a particular contaminant during this time period. At the end of the period and collecting layer is analyzed. The higher molecular flux at the collector allows concentration of contaminants into collecting materials such as activated charcoal, Chromasorb ® 102 (Johns-Manville), XAD-2, and XAD-4 sorbents (Rohm & Haas). On the other hand, the reduction in molecular flux into the collection layer allows high concentrations of contaminant to be monitored without overloading the sorbent. Analytical techniques include gas chromatography, mass spectroscopy, infra-red and others and the compound can be eluted for analysis thermally or by elution solvents such as $CS_2$. Colorimetric reactions can be analyzed by comparisons with known color standards or by densitometry.

The invention is further illustrated by the following non-limiting examples:

EXAMPLE 1

A device was constructed similar to that illustrated in FIGS. 13 and 14 with twenty conical chambers wherein the ratios of the diameter at the chamber entrance to the diameter at the collecting layer are varied. The chamber thickness was ten millimeters. The chamber entrances were covered with Celgard ® (Celenese), a microporous polypropylene. A hydrogen sulfide collecting layer was prepared by dipping No. 5 Whatman paper into a 1% solution of lead naphthenate in methyl ethyl ketone. After drying, a portion of the treated paper was placed in the above multi-chamber device and exposed to air with 12 ppm of hydrogen sulfide for varing period of time. A fresh piece of treated paper was utilized for each time period, and the exposures were 10, 15, 30 and 60 minutes. The treated paper developed a series of dark images which varied in intensity from chamber to chamber as a result of hydrogen sulfide exposure. The optical density of the filter paper in the chambers was measured with a Macbeth reflection densitometer. Five chambers had images which could not be measured with the above densitometer. From the above measurements, it was possible to accurately estimate the time when the image in each chamber reached an optical density of 50% of maximum. The sensitivity of each chamber is proportional to the ratio of the diameter of the chamber entrance hole ($d_1$) to the diameter of hole ($d_2$) contacting the collecting layer. The length of time necessary for a chamber to reach a selected optical density is inversely proportional to the sensitivity. In the following Table I, the time to reach 50% of the maximum optical density is tabulated for each chamber. The sensitivity ($d_1/d_2 = r$) of each chamber and the reciprocal of the sensitivity ($d_2/d_1 = 1/r$) are also tabulated. The data are plotted in FIG. 16.

TABLE I

| Chamber No. | $d_1$ (mm) | Sensitivity (r) | Reciprocal of Sensitivity (1/r) | Exposure Time (Minutes) |
|---|---|---|---|---|
| 1 | 2.3 | .23 | 4.4 | 61 |
| 2 | 2.8 | .28 | 3.6 | 50 |
| 3 | 3.0 | .30 | 3.3 | 46 |
| 4 | 3.3 | .33 | 3.0 | 38 |
| 5 | 3.8 | .38 | 2.6 | 32 |
| 6 | 4.3 | .43 | 2.3 | 28 |
| 7 | 5.1 | .51 | 2.0 | 24 |
| 8 | 5.7 | .57 | 1.8 | 21 |
| 9 | 6.4 | .64 | 1.6 | 19 |
| 10 | 7.2 | .72 | 1.4 | 16 |
| 11 | 8.9 | .89 | 1.1 | 13 |
| 12 | 10.0 | 1.00 | 1.0 | 10 |
| 13 | 10.0 | 1.22 | .8 | 8 |
| 14 | 10.0 | 1.64 | .6 | 6 |
| 15 | 10.0 | 2.38 | .4 | 3 |

As illustrated in FIG. 16, the time to a selected optical density is a linear function of the reciprocal of the sensitivity ($d_2/d_1$).

EXAMPLE 2

A multi-chamber device similar to the device illustrated in FIGS. 9–12 was constructed. The device contained 15 cylindrical cells. The thickness of plate 114 was 1.1 mm and plate 116 was 13.6 mm. A hydrogen sulfide collecting layer was prepared by dipping No. 5 Whatman filter paper into a solution containing 2% silver nitrate, 1% nitric acid, 5% glycerol and 20% methanol solution. After drying, the portions of the treated paper were placed in the above multi-chambered device and exposed for varying time periods to air containing 40 ppm hydrogen sulfide. The optical densities of the darkened image at each chamber were measured with the reflection densitometer.

It was found that the sensitivity of the device with cylindrical chambers was proportional to the square of the ratio of the diameter of the hole at the entrance ($d_1$) to the diameter of the hole at the collecting layer ($d_2$). Therefore, the time of exposure required for each chamber to reach a selected optical density is proportional to the reciprocal of the square of the ratio of $d_1/d_2$.

The exposure times required for the images to reach 85% of the maximum optical density are tabulated in the following Table II. The sensitivity, expressed by the ratio of $d_1/d_2$, and the square of the ratio $(d_1/d_2)^2$ are also given. In addition, the reciprocal of each of the above ratios are tabulated. The data are plotted in FIG. 17.

TABLE II

| Chamber Number | $d_1$ (mm) | Sensitivity | | Reciprocal of Sensitivity | | Exposure Time (Minutes) |
|---|---|---|---|---|---|---|
| | | $(d_1/d_2)$ | $(d_1/d_2)^2$ | $(d_2/d_1)$ | $(d_2/d_1)^2$ | |
| 1 | 1.1 | .11 | .012 | 9.1 | 82.6 | 573 |
| 2 | 1.3 | .13 | .017 | 7.7 | 59.2 | 425 |
| 3 | 1.7 | .17 | .029 | 5.9 | 34.6 | 278 |
| 4 | 2.0 | .20 | .040 | 5.0 | 25.0 | 215 |
| 5 | 2.5 | .25 | .063 | 4.0 | 16.0 | 163 |
| 6 | 2.8 | .28 | .078 | 3.6 | 12.8 | 143 |
| 7 | 3.2 | .32 | .102 | 3.1 | 9.8 | 123 |
| 8 | 3.6 | .36 | .130 | 2.8 | 7.7 | 108 |
| 9 | 4.3 | .43 | .185 | 2.3 | 5.4 | 95 |
| 10 | 5.0 | .50 | .250 | 2.0 | 4.0 | 88 |
| 11 | 5.6 | .56 | .314 | 1.8 | 3.2 | 80 |
| 12 | 6.3 | .63 | .397 | 1.6 | 2.5 | 78 |
| 13 | 7.1 | .71 | .504 | 1.4 | 2.0 | 73 |
| 14 | 8.4 | .83 | .689 | 1.2 | 1.5 | 70 |
| 15 | 10.0 | 1.00 | 1.000 | 1.0 | 1.0 | 68 |

As illustrated in FIG. 17, the time to the selected optical density is a linear function of the square of the ratio of $d_2/d_1$.

EXAMPLE 3

Figure 8:
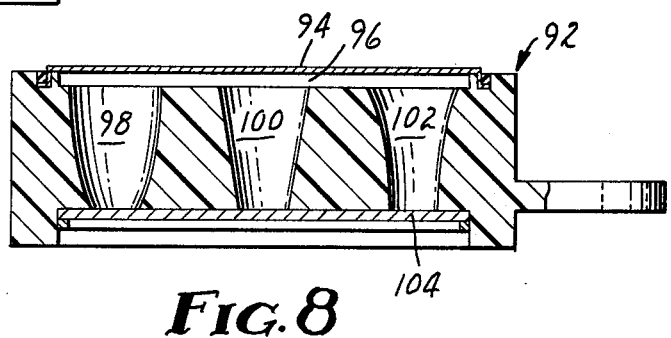
FIG. 8 is a sectional view taken along lines 8—8 of FIG. 7.

An experiment was conducted to demonstrate the effect of changes in the shape of the chamber. A device similar to that shown in FIG. 8 was constructed with three chambers. The large ends were all 1.05 cm and the small ends were all 0.25 cm in diameter. The thickness of each chamber was 1.0 cm.

One of the chambers was truncated conical-shaped, another was "trumpet" shaped and the third was "bullet" shaped.

The device was tested using $H_2S$ indicator paper described in Example 1. In one test, the larger aperture contacted the collecting layer ($H_2S$ indicator paper), and in a second test the samller apertures contacted the collecting layer. The results, obtained as optical density reading from a reflection densitometer, were as follows:

Large apertures toward collecting layer:

| | Bullet | Cone | Trumpet |
|---|---|---|---|
| 12 ppm for 30 min. | 0.16 | .11 | .07 |
| Small apertures toward collecting layer: | | | |
| 12 ppm for 6 min. | 0.44 | .38 | .28 |

In both cases, the "trumpet"-shaped chamber imaged the slowest and the "bullet"-shaped chamber imaged the fastest.

EXAMPLE 4

This example shows the increase in sensitivity resulting from a reduction in the area of a gold collecting layer which detects mercury atoms by changes in electrical conductivity. Monitors utilizing a gold film to detect mercury vapor are described in detail on U.S. Pat. No. 3,924,219.

Four monitoring devices (3M Brand Mercury Vapor Monitor No. 3600) utilizing a gold film about 0.015 μm thick, 3.3 mm wide and about 14.0 mm long were prepared, the film being deposited in a serpentine pattern on a smooth polystyrene surface. The gold surface was aligned with a serpentine shaped channel having width and total length equal to that of the gold surface. The depth of the channel was about 6.6 mm. A Celgard ® attenuating layer was attached across the channel opening.

Five other monitors were prepared identically except the gold surface was only 0.7 mm wide. Therefore, the surface area available for interaction with mercury atoms was reduced to about 21 percent of the area of the wider films used in the first group of monitors.

When these two groups of monitors were given identical exposure to 0.9935 mg mercury per cubic meter of air for 3.02 hours, the first group produced an average resistance change of 3.75 percent while the second group, having the more narrow gold film, produced a resistance change of 8.32 percent. In terms of the absolute sensitivity ratio, the monitors utilizing the smaller gold area produced a response 2.22 times that of the other monitors. Therefore, they could be used at correspondingly lower mercury concentrations.

What is claimed is:

1. A device for measuring the amount of at least one selected component of a fluid mixture comprising:
   (a) a collecting layer having a frontal surface area for collecting the selected component;
   (b) a base supporting the collecting layer;
   (c) barrier means for enclosing said collecting layer and defining at least one chamber having an entrance through which said fluid mixture diffuses into said chamber, and providing a substantially placid layer of fluid within said chamber, wherein the ratio of said chamber entrance area to said frontal surface area of said collecting layer is predetermined to provide a nonlinear gradient of said selected component within said chamber and affording molecular transport within said chamber between said chamber entrance and said collecting layer which is one of convergence, divergence and both.

2. A device for measuring the amount of at least one selected component of a fluid mixture comprising:
   (a) a collecting layer having a frontal surface area for collecting the selected component;
   (b) a base supporting said collecting layer;
   (c) a body member formed with wall means defining at least one chamber having opposed ends and a varying cross-section therebetween to converge toward one of said ends, said collecting layer being disposed at one of said ends and a porous attenuating layer being disposed adjacent the other of said ends whereby said fluid within said chamber is substantially placid, said chamber having a nonlinear concentration gradient of said selected component within said chamber affording molecular transport within said chamber between the ends thereof toward said collecting layer which is one of convergence, divergence and both.

3. The device according to claim 2 wherein said chamber comprises a plurality of generally cylindrical sections the diameters of which decrease toward said collecting layer.

4. The device according to claim 2 wherein said chamber comprises a plurality of generally cylindrical sections the diameters of which increase toward said collecting layer.

5. The device according to claim 2 wherein said chamber has the shape of a trucated cone.

6. The device according to claim 2 wherein said chamber is trucated ovate shaped in vertical section.

7. The device according to claim 2 wherein said chamber in vertical section has opposed convex walls.

8. The device according to claim 2 wherein said wall means define a plurality of chambers each having a different sensitivity.

9. The device according to claim 8 wherein said collecting layer changes color upon collecting a predetermined amount of the selected component.

10. The device according to claim 9 wherein said base further comprises hinge means allowing visualization of said collecting layer.

11. The device according to claim 9 wherein said base is transparent.

12. The device according to claim 8 wherein most of said chambers comprise a plurality of generally cylindrical sections of different cross-sectional areas.

13. The device according to claim 8 wherein most of said chambers are trucated conical shaped.

* * * * *